United States Patent
Barrett et al.

(10) Patent No.: US 6,609,025 B2
(45) Date of Patent: Aug. 19, 2003

(54) TREATMENT OF OBESITY BY BILATERAL SUB-DIAPHRAGMATIC NERVE STIMULATION

(75) Inventors: Burke T. Barrett, Houston, TX (US); Mitchell S. Roslin, New York, NY (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 09/753,758

(22) Filed: Jan. 2, 2001

(65) Prior Publication Data

US 2002/0087192 A1 Jul. 4, 2002

(51) Int. Cl.[7] .................................................. A61N 1/00
(52) U.S. Cl. ........................................... 607/2; 607/118
(58) Field of Search .............................. 607/2, 13, 14, 607/118, 133, 40, 45; 600/319, 38, 13, 29, 201, 207, 377; 128/DIG. 25, 898

(56) References Cited

U.S. PATENT DOCUMENTS

| | | | |
|---|---|---|---|
| 5,188,104 A | 2/1993 | Wernicke et al. | 607/44 |
| 5,231,988 A * | 8/1993 | Wernicke et al. | 607/2 |
| 5,263,480 A * | 11/1993 | Wernicke et al. | 607/133 |
| 5,330,507 A | 7/1994 | Schwartz | 607/14 |
| 5,423,872 A | 6/1995 | Cigaina | 607/40 |
| 5,514,175 A | 5/1996 | Kim et al. | 607/136 |
| 5,540,730 A | 7/1996 | Terry, Jr. et al. | 607/40 |
| 5,540,734 A | 7/1996 | Zabara | 607/46 |
| 5,690,691 A | 11/1997 | Chen et al. | 607/40 |
| 5,707,400 A * | 1/1998 | Terry et al. | 607/44 |
| 5,792,210 A | 8/1998 | Wamubu et al. | 607/58 |
| 5,913,876 A | 6/1999 | Taylor et al. | 607/2 |
| 5,938,584 A * | 8/1999 | Ardito et al. | 600/38 |
| 6,086,525 A * | 7/2000 | Davey et al. | 128/DIG. 25 |
| 6,269,269 B1 * | 7/2001 | Ottenhoff et al. | 607/42 |
| 6,360,750 B1 * | 3/2002 | Gerber et al. | 128/898 |

* cited by examiner

Primary Examiner—Tu Ba Hoang
(74) Attorney, Agent, or Firm—Blank Rome LLP

(57) ABSTRACT

A method and apparatus for treating obese or other patients with compulsive overeating disorder includes unilaterally or bilaterally stimulating one or both of the left and right branches of a patient's vagus nerve directly or indirectly with an electrical pulse signal generated by an implantable neurostimulator with at least one operatively coupled nerve electrode to apply the pulse signal to the selected nerve branch at a location below the patient's diaphragm. The implantable neurostimulator is programmable to enable physician programming of electrical and timing parameters of the pulse signal, to induce weight loss of the patient.

10 Claims, 2 Drawing Sheets

TREATMENT OF OBESITY BY BILATERAL SUB-DIAPHRAGMATIC NERVE STIMULATION

CROSS-REFERENCE TO RELATED APPLICATIONS

This application is related to U.S. application Ser. No. 09/346,396, filed Jul. 1, 1999 (referred to elsewhere in this application as "the '396 application"), assigned to the same assignee as the present application.

BACKGROUND OF THE INVENTION

The present invention relates generally to methods and apparatus for treating eating disorders by application of modulating electrical signals to a selected cranial nerve, nerve branch or nerve bundle, and more particularly to techniques for treating patients with overeating disorders, especially obese patients, by application of such signals unilaterally or bilaterally to the patient's vagus nerve with one or more neurostimulating devices.

Increasing prevalence of obesity is one of the most serious and widespread health problems facing the world community. It is estimated that, currently, about 6% of the total population of the United States is morbidly obese and a much larger percentage is either obese or significantly overweight. Morbid obesity is defined as having a body mass index of more than forty, or, as is more commonly understood, being more than one hundred pounds overweight for a person of average height. Aside from what may be an epidemic of obesity, it is believed by many health experts that obesity is one of the first two leading causes of preventable deaths in the United States, either ahead of or just behind cigarette smoking.

Whether or not that is an accurate assessment, studies have indicated that morbid obesity dramatically increases health care costs. It is a major cause of adult onset diabetes in the United States, up to approximately eighty percent of the cases. It may be a leading factor in as many as ninety percent of sleep apnea cases. Obesity is also a substantial risk factor for coronary artery disease, stroke, chronic venous abnormalities, numerous orthopedic problems and esophageal reflux disease. Researchers have documented a link between obesity, infertility and miscarriages, as well as post menopausal breast cancer.

The classical treatment option for obese people combines nutritional counseling with exercise and education, but has demonstrated relatively little long term success. Liquid diets and pharmaceutical agents can bring about acute, but not lasting weight loss. Surgical procedures for either gastric restriction or malabsorption in cases of severe obesity have shown the greatest success long-term, but are major surgery that can lead to emotional problems, and have their share of failures (e.g., Kriwanek, "Therapeutic failures after gastric bypass operations for morbid obesity," *Langenbecks Archiv. Fur Chirurgie*, 38(2): 70–74, 1995).

U.S. Pat. No. 5,263,480 to J. Wernicke et al., assigned to the same assignee as the present application, discloses treatment for eating disorders including obesity and compulsive overeating disorder by selectively applying modulating electrical signals to the patient's vagus nerve, preferably using an implanted neurostimulator. Modulating signals may be used to stimulate vagal activity to increase the flow of neural impulses up the nerve, or to inhibit vagal activity to block neural impulses from moving up the nerve, toward the brain, for producing excitatory or inhibitory neurotransmitter release.

Both of these cases of modulating the electrical activity of the vagus nerve have been termed vagus nerve stimulation, or VNS. The '480 patent theorized that VNS could be used for appetite suppression by causing the patient to experience satiety, a sensation of "fullness" of the stomach which would result in decreased food consumption and consequent weight reduction. For example, the stimulus generator of the neurostimulator is implanted in a convenient location in the patient's body, attached to an electrical lead having a nerve electrode implanted on the vagus nerve or branch thereof in the esophageal region slightly above the stomach. If the patient's food consumption over a given period exceeded a predetermined threshold level, detected and measured for example by sensing electrodes implanted at or near the esophagus, the stimulus generator is triggered to apply VNS and thereby induce satiety. Alternatively, VNS is applied periodically during the patient's normal waking hours except in periods of prescribed mealtimes, or is applied as a result of patient intervention by manual activation of the stimulus generator using external magnet control. Patient intervention assumes a patient with an earnest desire to control his or her eating behavior, but normally lacking will power to control the compulsive behavior without the support of VNS.

Like most of the pairs of cranial nerves, the tenth cranial nerve, the vagus, originates from the brain stem. It passes through foramina of the skull to parts of the head, neck and trunk. The vagus is a mixed nerve, with both sensory and motor fibers, the sensory fibers being primary and attached to neuron cell bodies located outside the brain in ganglia groups, and the motor fibers attached to neuron cell bodies located within the gray matter of the brain. The vagus, as a cranial nerve, is part of the peripheral nervous system or PNS whose nerves branch out from the central nervous system (CNS) to connect the CNS to other body parts. Somatic fibers of the cranial nerves are involved in conscious activities and connect the CNS to the skin and skeletal muscles, while autonomic fibers of these nerves are involved in unconscious activities and connect the CNS to the visceral organs such as the heart, lungs, stomach, liver, pancreas, spleen, and intestines.

The motor fibers of the vagus nerve transmit impulses to the muscles associated with speech and swallowing, the heart, and smooth muscles of the visceral organs of the thorax and abdomen. In contrast, its sensory fibers transmit impulses from the pharynx, larynx, esophagus and visceral organs of the thorax and abdomen. The vagus is split into left and right branches, or left and right vagi, which run respectively through the left and right sides of the neck and trunk. It is the axial portion of the body, which includes the head, neck and trunk with which we are primarily concerned in respect of the present invention. The ventral cavity of the axial portion contains visceral organs and includes the thoracic cavity and the abdominopelvic cavity, which are separated by the diaphragm, a broad thin muscle. Visceral organs in the thoracic cavity include the right and left lungs, the heart, the esophagus, the trachea and the the thymus gland. Below the diaphragm, in the abdominopelvic cavity and specifically the upper abdominal portion or abdominal portion, the visceral organs therein include the stomach, liver, spleen, gall bladder, and majority of the small and large intestines.

The vagus nerve is the dominant nerve of the gastrointestinal (GI) tract, the right and left branches or nerve afferents of the vagus connecting the GI tract to the brain. After leaving the spinal cord, the vagal afferents transport information regarding that tract to the brain. In the lower part of the chest, the left vagus rotates, becomes the anterior vagus, and innervates the stomach. The right vagus rotates to become the posterior vagus, which branches into the celiac division and innervates the duodenum and proximal intestinal tract.

The exact mechanisms leading an individual to satiety are not fully known, but a substantial amount of information has been accumulated. Satiety signals include the stretch of mechanoreceptors, and the stimulation of certain chemosensors (e.g., "*A Protective Role for Vagal Afferents: An Hypothesis,*" Neuroanatomy and Physiology of Abdominal Vagal Afferents, Chapter 12, CRC Press, 1992). These signals are transported to the brain by the nervous system or endocrine factors such as gut peptides (e.g., "*External Sensory Events and the Control of the Gastrointestinal Tract: An Introduction,*" id. at Chapter 5). It has been demonstrated that direct infusion of maltose and oleic acid into the duodenum of rats leads to a reduction in food intake, and that the response is ablated by vagotomy or injection of capsaicin, which destroys vagal afferents. Introduction of systemic cholecystokinin also reduces intake in rats, and is ablated by destruction of vagal afferents.

While the vagus is often considered to be a motor nerve which also carries secretory signals, 80% of the nerve is sensory consisting of afferent fibers (e.g., Grundy et al., "*Sensory afferents from the gastrointestinal tract,*" Handbook of Physiology, Sec. 6, S.G., Ed., *American Physiology Society*, Bethesda, Md., 1989, Chapter 10).

The aforementioned '396 application discloses a method of treating patients for obesity by bilateral stimulation of the patient's vagus nerve (i.e., bilateral VNS) in which a stimulating electrical signal is applied to one or both branches of the vagus. The parameters of the signal are predetermined to induce weight loss of the patient. The signal is preferably a pulse signal applied at a set duty cycle (i.e., its on and off times) intermittently to both vagi. In any event, VNS is applied at a supra-diaphragmatic position (i.e., above the diaphragm) in the ventral cavity. The electrical pulse stimuli are set at a current magnitude below the retching level of the patient (e.g., not exceeding about 6 milliamperes (mA), to avoid patient nausea) in alternating periods of continuous application and no application. Pulse width is set at or below 500 microseconds ($\mu$s), and pulse repetition frequency at about 20–30 Hz. The on/off duty cycle (i.e., first period/second period of the alternating periods) is programmed to a ratio of about 1:1.8. The neurostimulator, which may be a single device or a pair of devices, is implanted and electrically coupled to lead(s) having nerve electrodes implanted on the right and left branches of the vagus.

SUMMARY OF THE INVENTION

According to the present invention, a method of treating patients for obesity comprises unilateral or bilateral stimulation of the left and right vagi at a sub-diaphragmatic position (i.e., below the diaphragm) in the ventral cavity, rather than at a supra-diaphragmatic position as taught by the '396 application. The stimulating electrical signal is preferably applied to the vagus two to three inches below the diaphragm, and may be applied either synchronously or asynchronously to both the right and left branches, preferably in the form of a series of pulses applied intermittently to both branches according to a predetermined on/off duty cycle. The intermittent application is preferably chronic, rather than acute. However, continuous application or acute application by bilateral stimulation of the right and left vagi or unilateral stimulation of either branch, at the sub-diaphragmatic position, is also contemplated.

The sub-diaphragmatic application of VNS may have an enhanced effect in inducing satiety in the patient, being in closer proximity to the stomach itself. Certainly, in the case of neurostimulator device implantation superficially in the abdominal region of the patient, the sub-diaphragmatic application has an advantage of enabling shorter leads for the nerve electrode(s). Additionally, application of the neurostimulator may be more easily accomplished with this approach as opposed to a supra-diaphragmatic approach which requires accessing the vagi in the chest cavity.

Acute application of the stimulating electrical signal to the right and left vagi during a customary mealtime, or from a short time preceding and/or following the mealtime, according to the patient's circadian cycle, may be effective in certain cases. Automatic delivery of bilateral intermittent stimulation is preferred, but it is alternatively possible to control application of the stimulating electrical signal to the right and left vagi by an external commencement signal produced by the patient's placement of an external magnet, or by another patient-applied signal, in proximity to the location of the implanted device.

Preferably, the same stimulating electrical signal is applied to both the right and left vagi, but as an alternative, a stimulating electrical signal might be applied to the right vagus which is different from the stimulating electrical signal applied to the left vagus. And although two separate nerve stimulator generators may be implanted for stimulating the left and right vagi, respectively, as an alternative a single nerve stimulator generator may be implanted for bilateral stimulation if the same signal is to be applied to both the left and right branches of the vagus nerve, whether delivered synchronously or asynchronously to the vagi.

As with the method disclosed in the '396 application, the current magnitude of the stimulating signal is programmed to be less than about 6 mA, and in any case is held below the retching level of the patient as determined by the implanting physician at the time the implant procedure is performed, or shortly thereafter. This is important to avoid patient nausea during periods of vagus nerve stimulation. Preferably, the pulse width is set to a value not exceeding about 500 $\mu$s, the pulse repetition frequency is set at about 20–30 Hertz (Hz), the VNS regimen follows alternating periods of stimulation and no stimulation, with the second period about 1.8 times the length of the first period in the alternating sequence (i.e., the on/off duty cycle is 1:1.8).

The apparatus of the present invention for treating obese patients suffering from eating disorders includes an implanted neurostimulator for simultaneously stimulating left and right branches of the patient's vagus nerve via separate lead/electrodes operatively coupled to the neurostimulator and implanted on the right and left vagi in a sub-diaphragmatic position, the stimulation being applied continuously during a first period, alternating with no stimulation during a second period, throughout the prescribed duration of the stimulation regimen.

Accordingly, it is a principal objective of the present invention to provide methods and apparatus for treating and controlling the overeating disorder, especially in obese patients, by means of bilateral electrical stimulation of the patient's right and left vagi at a sub-diaphragmatic location.

Another aim of the invention is to provide methods of treating and controlling compulsive overeating and obesity by bilateral intermittent electrical pulse stimulation of right and left vagi at a sub-diaphragmatic position in the patient.

Alternative techniques include indirect stimulation of the vagus, either bilaterally or unilaterally, at a location near one or both branches of the nerve or elsewhere, which has the effect of stimulating the vagus nerve as well. This may be accomplished through afferents or efferents, for example.

It is also contemplated that direct or indirect unilateral or bilateral stimulation applied at or by way of a sub-diaphragmatic location of one or more of the other cranial nerves of suitable sensory, motor or mixed fiber types may be effective in treating compulsive overeating disorder, as an alternative to vagus nerve stimulation.

Some differences may be observed from stimulator to stimulator in magnitude of current in the pulses of the stimulation signal, and may be attributable to things such as patient impedance, variation of the vagus nerve from right to left or between patients, and variation in contact between the vagus and the electrode implanted thereon from implant to implant.

According to other aspects of treatment by stimulation of the vagus or other suitable cranial nerve in the vicinity of the patient's diaphragm, beneficial weight reduction is aided by increased activity attributable to release of norepinephrine, serotonin or other mechanisms, increased metabolism and change in gastric motility. This therapy may also have beneficial effect in treatment of other disorders such as type II diabetes, high blood pressure and orthopedic problems which typically co-exist with compulsive overeating disorder and obesity.

BRIEF DESCRIPTION OF THE DRAWINGS

The above and still further aims, objectives, aspects, features and attendant advantages of the present invention will be better understood from a consideration of the following detailed description of a presently contemplated best mode of practicing the invention, by reference to a preferred exemplary method and embodiment thereof, taken in conjunction with the accompanying Figures of drawing, in which.

DESCRIPTION OF THE PRESENTLY CONTEMPLATED BEST MODE

A generally suitable form of neurostimulator for use in the apparatus and method of the present invention is disclosed, for example, in U.S. Pat. No. 5,154,172, assigned to the same assignee as the instant application (the device also referred to from time to time herein as a NeuroCybernetic Prosthesis or NCP device (NCP is a trademark of Cyberonics, Inc. of Houston, Tex., the assignee)). Certain parameters of the electrical stimuli generated by the neurostimulator are programmable, preferably by means of an external programmer (not shown) in a conventional manner for implantable electrical medical devices.

Figure 1:
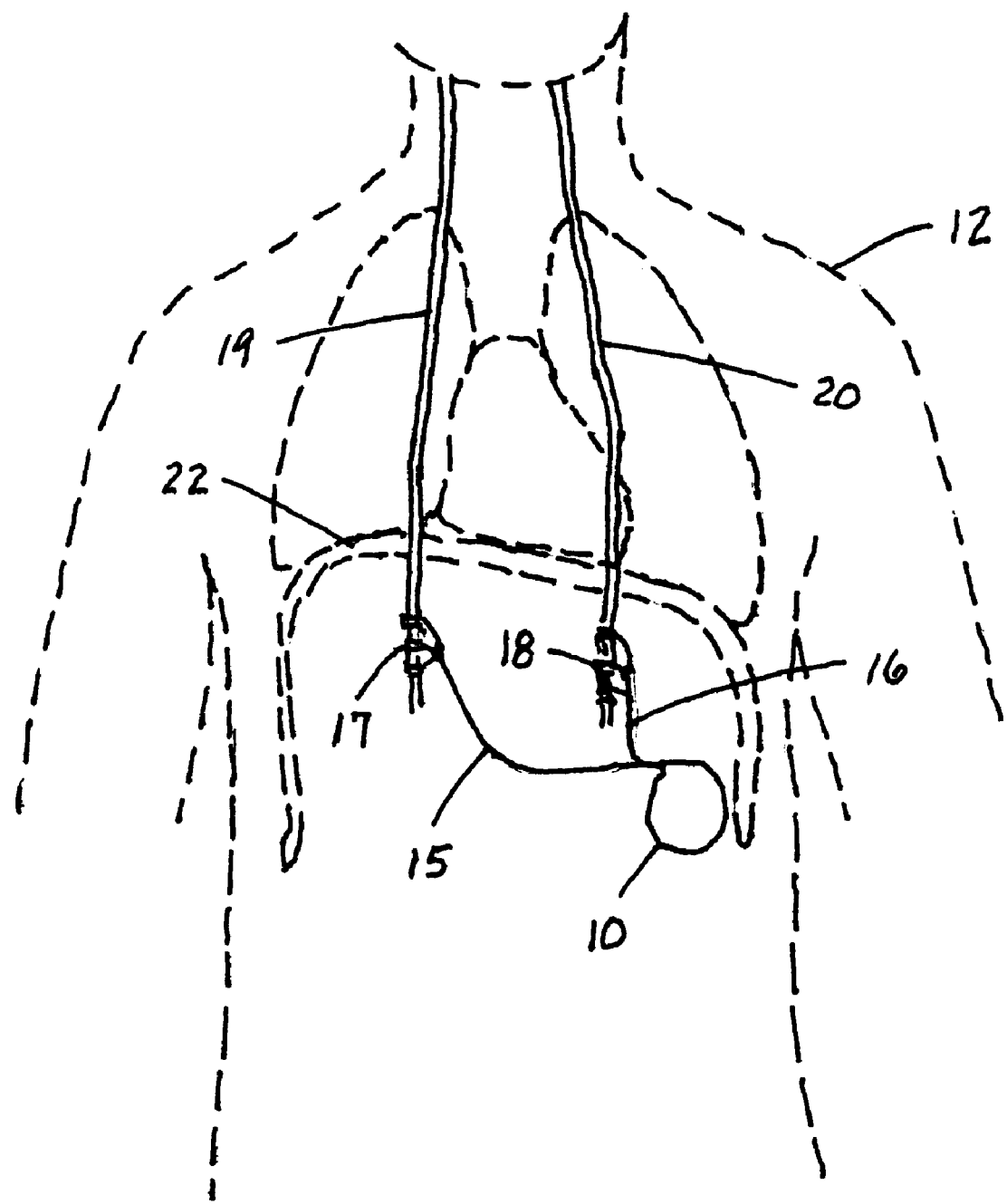
FIG. 1 is a simplified partial front view of a patient (in phantom) having an implanted neurostimulator for generating the desired signal stimuli which are applied directly and bilaterally at sub-diaphragmatic location to the right and left branches of the patient's vagus via an implanted lead/nerve electrode system electrically connected to the neurostimulator.

Referring to FIG. 1, the neurostimulator, identified in the drawing by reference number 10 is implanted in a patient 12, preferably in the abdominal region, for example, via a left laparotomy incision. For the preferred implementation and method of direct bilateral stimulation, lead-electrode pair 15, 16 is also implanted during the procedure, and the proximal end(s) of the lead(s) electrically connected to the neurostimulator. The lead-electrode may be of a standard bipolar lead nerve electrode type available from Cyberonics, Inc.

According to the preferred method of the invention, the nerve electrodes 17, 18 are implanted on the right and left branches 19, 20, respectively, of the patient's vagus nerve at a sub-diaphragmatic location. The nerve electrodes are equipped with tethers for maintaining each electrode in place without undue stress on the coupling of the electrode onto the nerve itself. Preferably, the sub-diaphragmatic location of this coupling is approximately two to three inches below the patient's diaphragm 22 for each branch 19, 20.

Neurostimulator 10 generates electrical stimuli in the form of electrical impulses according to a programmed regimen for bilateral stimulation of the right and left branches of the vagus. During the implant procedure, the physician checks the current level of the pulsed signal to ascertain that the current is adjusted to a magnitude at least slightly below the retching threshold of the patient. Typically, if this level is programmed to a value less than approximately 6 mA, the patient does not experience retching attributable to VNS although variations may be observed from patient to patient. In any event, the maximum amplitude of the current should be adjusted accordingly until an absence of retching is observed, with a suitable safety margin. The retching threshold may change noticeably with time over a course of days after implantation, so the level should be checked especially in the first few days after implantation to determine whether any adjustment is necessary to maintain an effective regimen.

The bilateral stimulation regimen of the VNS preferably employs an intermittent pattern of a period in which a repeating series of pulses is generated for stimulating the nerve, followed by a period in which no pulses are generated. The on/off duty cycle of these alternating periods of stimulation and no stimulation preferably has a ratio in which the off time is approximately 1.8 times the length of the on time. Preferably also, the width of each pulse is set to a value not greater than about 500 μs, and the pulse repetition frequency is programmed to be in a range of about 20 to 30 Hz. The electrical and timing parameters of the stimulating signal used for VNS as described herein for the preferred embodiment will be understood to be merely exemplary and not as constituting limitations on the scope of the invention.

The patient's eating behavior should be allowed to stabilize at approximately the preoperative level before the VNS regimen is actually administered. Treatment applied in the form of chronic intermittent bilateral nerve stimulation over each twenty-four hour period may be observed initially to result in no change in eating behavior of the patient. But after a period of several days of this VNS regimen, a discernible loss of interest in heavy consumption of food should occur. A typical result would be that mealtime consumption tends to stretch over a considerably longer period of time than that observed for the patient's preoperative behavior, with smaller quantities of food intake separated by longer intervals of no consumption in the course of a single meal. The VNS treatment should not affect normal behavior in other aspects of the patient's life. A complete suspension of the VNS regimen would result in a relatively rapid return to the previous overeating behavior, ending after resumption of the VNS regimen. Observations appear to indicate that treatment by bilateral stimulation may be safe and effective in changing eating patterns and behavior in obese human patients, and more generally in human patients suffering from compulsive overeating disorder.

Animal testing using bilateral VNS has tended to demonstrate that slowed eating and apparent lack of enthusiasm in food consumption is centrally mediated and the result of a positive response of inducing a sensation of satiety mimicking that which would occur after consumption of a full meal, rather than of a negative response of nausea or sick stomach.

The intermittent aspect of the bilateral stimulation resides in applying the stimuli according to a prescribed duty cycle. The pulse signal is programmed to have a predetermined on-time in which a train or series of electrical pulses of preset parameters is applied to the vagus branches, followed by a predetermined off-time. Nevertheless, continuous application of the electrical pulse signal may also be effective in treating compulsive overeating disorder.

Figure 2:
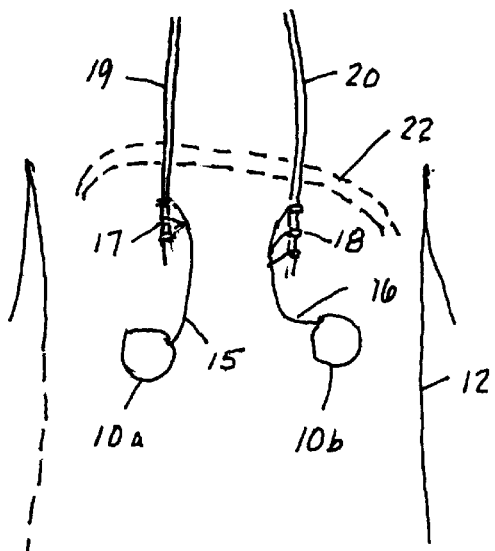
FIG. 2 is a simplified partial front view of a patient similar to that of FIG. 1, but in which a pair of implanted neurostimulators is used for generating the desired signal stimuli.

Also, as shown in FIG. 2, dual implanted NCP devices 10a and 10b may be used as the pulse generators, one supplying the right vagus and the other the left vagus to provide the bilateral stimulation. At least slightly different stimulation for each branch may be effective as well. Use of implanted stimulators for performing the method of the invention is preferred, but treatment may conceivably be administered using external stimulation equipment on an outpatient basis, albeit only somewhat less confining than complete hospitalization. Implantation of one or more neurostimulators, of course, allows the patient to be completely ambulatory, so that normal daily routine activities including on the job performance is unaffected.

Figure 3:
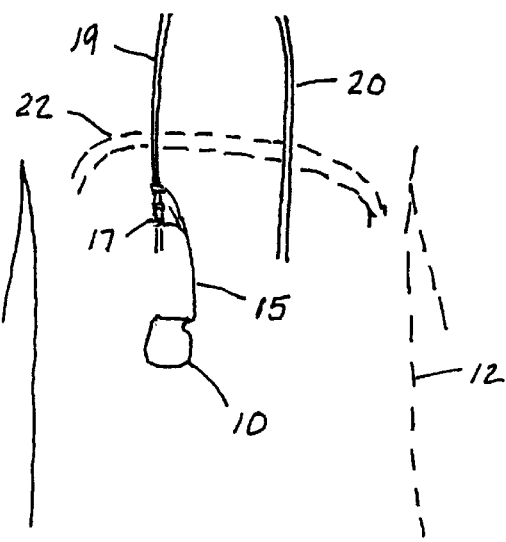
FIG. 3 is a simplified partial front view of a patient in which an implanted neurostimulator and associated electrode is used for unilateral stimulation of only one branch of the vagus nerve.

The desired stimulation of the patient's vagus nerve may also be achieved by performing unilateral sub-diaphragmatic stimulation of either the left branch or the right branch of the vagus nerve, as shown in FIG. 3. A single neurostimulator 10 is implanted together with a lead 15 and associated nerve electrode 17. The nerve electrode 17 is implanted on either the right branch 19 or the left branch 20 of the nerve, preferably in a location in a range of from about two to about three inches below the patient's diaphragm 22. The electrical signal stimuli are the same as described above.

Figure 4:
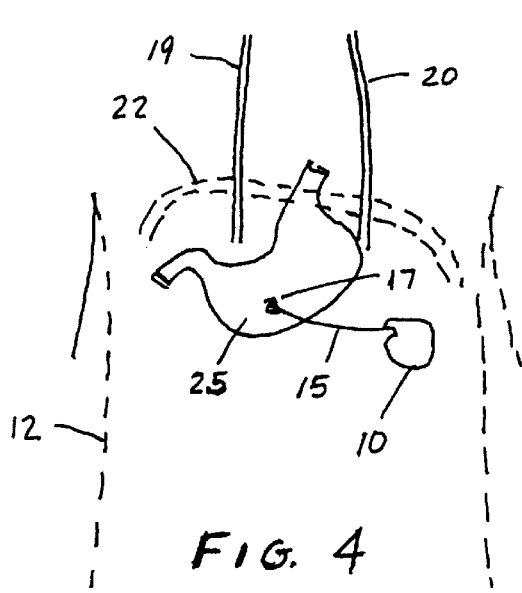
FIG. 4 is a simplified partial front view of a patient in which the signal stimuli are applied at a portion of the nervous system remote from the vagus nerve such as at or near the stomach wall, for indirect stimulation of the vagus nerve.

In a technique illustrated in FIG. 4, the signal stimuli are applied at a portion of the nervous system remote from the vagus nerve such as at or near the stomach wall 25, for indirect stimulation of the vagus nerve in the vicinity of the sub-diaphragmatic location. Here, at least one signal generator 10 is implanted together with one or more electrodes 17 subsequently operatively coupled to the generator via lead 15 for generating and applying the electrical signal internally to a portion of the patient's nervous system other than the vagus nerve, to provide indirect stimulation of the vagus nerve in the vicinity of the desired location. Alternatively, the electrical signal stimulus may be applied non-invasively to a portion of the patient's nervous system for indirect stimulation of the vagus nerve at a sub-diaphragmatic location.

Figure 5:
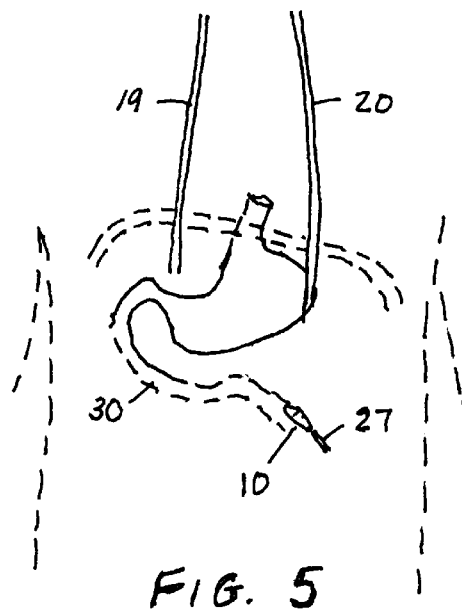
FIG. 5 is a simplified partial front view of a patient in which the signal stimuli are applied remotely from electrical stimulating device placed by an endoscope from an area composing the GI tract.

In an arrangement shown in FIG. 5, the signal stimuli are applied remotely from electrical stimulating device 10 placed by an endoscope 27 from an area composing the GI tract 30.

It is again noted that the principles of the invention may be applicable to selected cranial nerves other than the vagus, to achieve the desired results. It will thus be seen that a variety of different techniques and arrangements may be employed to practice the invention. Accordingly, although a presently contemplated best mode and certain other modes of treating and controlling overeating disorders to induce weight loss in the patient through a regimen of cranial nerve, and more specifically vagus nerve, stimulation either directly or indirectly at a sub-diaphragmatic location has been described herein, variations and modifications may be made within the scope of the present invention. It is therefore desired that the invention be limited only as required by the following claims and by the rules and principles of the applicable law.

What is claimed is:

1. A method of treating obese patients by applying a therapy to reduce the patient's appetite, which comprises the step of bilaterally stimulating the left and right branches of the patient's vagus nerve with an electrical signal applied directly or indirectly to both of said branches at a location below the patient's diaphragm, including programming electrical and timing parameters of said electrical signal, to give the patient a sensation of satiety and thereby induce weight loss of the patient.

2. The method of claim 1, including implanting at least one signal generator and electrodes operatively coupled thereto for generating and applying said electrical signal to both of said branches of the vagus nerve at said location.

3. The method of claim 1, including implanting at least one signal generator and electrodes operatively coupled thereto for generating and applying said electrical signal internally to a portion of the patient's nervous system other than the vagus nerve to indirectly stimulate both of said branches of the vagus nerve at said location.

4. The method of claim 1, wherein said stimulating electrical signal comprises a sequence of electrical pulses.

5. The method of claim 1, wherein the step of bilaterally stimulating comprises applying said electrical signal to hot of said branches of the vagus nerve at a location in a range of from about two to about three inches below the patient's diaphragm.

6. The method of claim 1, wherein the step of bilaterally stimulating includes applying said electrical signal intermittently, in alternating on and off intervals according to a predetermined duty cycle.

7. The method of claim 1, wherein the step of bilaterally stimulating includes applying said electrical signal continuously.

8. The method of claim 1, wherein the step of bilaterally stimulating comprises applying said electrical signal synchronously to both of said branches of the vagus nerve.

9. The method of claim 1, wherein the step of bilaterally stimulating comprises applying said electrical signal endoscopically from a portion of the patient's gastrointestinal tract.

10. The method of claim 1, wherein the step of bilaterally stimulating comprises applying said electrical signal non-invasively to a portion of the patient's nervous system other than the vagus nerve to indirectly stimulate both of said branches of the vagus nerve at said location.

\* \* \* \* \*